Figure 1:
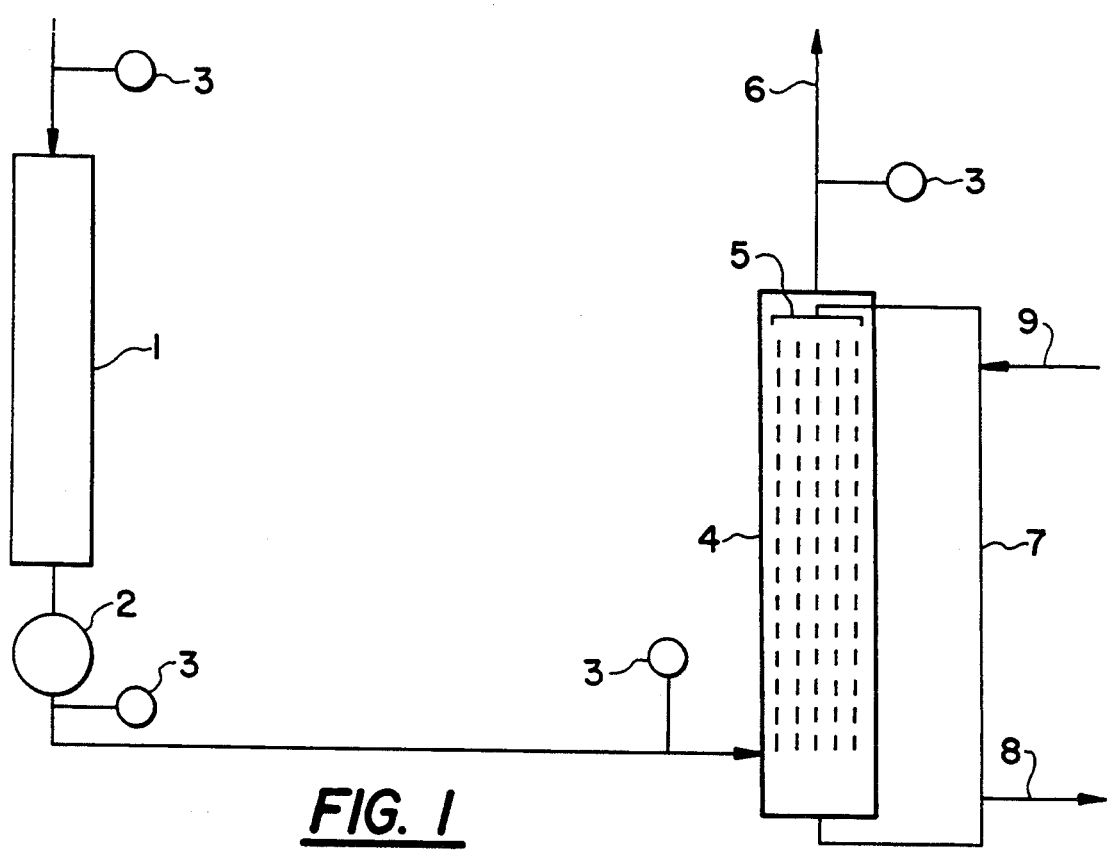

United States Patent [19]

Jennings et al.

[11] Patent Number: 5,384,420
[45] Date of Patent: Jan. 24, 1995

[54] PRODUCTION OF ETHYLENE OXIDE

[75] Inventors: James R. Jennings, Cleveland; Percy Hayden, Guisborough; Andrew J. Allchurch, Cleveland, all of England

[73] Assignee: Imperial Chemical Industries plc, London, England

[21] Appl. No.: 971,919

[22] PCT Filed: Jun. 18, 1991

[86] PCT No.: PCT/GB91/00975

§ 371 Date: Feb. 19, 1993

§ 102(e) Date: Feb. 19, 1993

[87] PCT Pub. No.: WO91/19705

PCT Pub. Date: Dec. 26, 1991

[30] Foreign Application Priority Data

Jun. 19, 1990 [GB] United Kingdom ............... 9013662
Apr. 8, 1991 [GB] United Kingdom ............... 9107345

[51] Int. Cl.$^6$ .................. C07D 301/32; C07D 303/04
[52] U.S. Cl. ...................................... 549/541; 549/538
[58] Field of Search ........................... 549/538, 541

[56] References Cited

U.S. PATENT DOCUMENTS

| | | | |
|---|---|---|---|
| Re. 25,933 | 12/1965 | Huckins | 549/538 |
| 4,469,492 | 9/1984 | Lagana et al. | 549/538 |
| 4,822,900 | 9/1989 | Hayden | 549/538 |
| 4,822,926 | 4/1989 | Dye | 568/867 |

FOREIGN PATENT DOCUMENTS 3642 8/1979 European Pat. Off. .
176253 4/1986 European Pat. Off. .

Primary Examiner—Joseph E. Evans
Attorney, Agent, or Firm—Cushman Darby & Cushman

[57] ABSTRACT

A gas stream from a reaction in which ethylene oxide is produced by reacting ethylene with oxygen which gas stream comprises oxides of nitrogen and steam the gas stream is cooled to condense water, condensed water is removed, and ethylene oxide is then recovered from the gas stream. A substantial amount of the oxides of nitrogen is removed from the gas stream during the condensation.

18 Claims, 1 Drawing Sheet

PRODUCTION OF ETHYLENE OXIDE

This invention relates to the production of ethylene oxide.

It is known from U.S. Pat. No. 4,822,920 to produce ethylene oxide by reacting ethylene with oxygen in the presence of a silver containing catalyst and a chlorine containing reaction modifier in the absence of nitrate and/or nitrite forming substances in the gas phase and to spray the gas stream flowing from the reactor with aqueous alkali. This cools the gas stream and removes impurities such as oxalic acid, aldehydes and aldol products. Some ethylene oxide is inevitably removed and at least partly hydrolysed to ethylene glycol during this step.

It is also known from our European Patent No 3642 that ethylene may be oxidised with oxygen to ethylene oxide in the presence of a silver containing catalyst and a nitrate or nitrite forming substance which is in the gas phase simultaneously with a chlorine containing reaction modifier. The gas stream from the reaction generally comprises unreacted materials, impurities, $H_2O$, oxides of nitrogen and other gases as well as ethylene oxide.

The oxides of nitrogen, though not dangerous in themselves tend to react with other components derived from the reaction in subsequent purification sections of process plant to produce solid or liquid organic nitrogen compounds which may accumulate in cold parts and represent an explosion hazard and/or contaminate the product of the process.

We have found that oxides of nitrogen and other nitrogen containing compounds can be removed by condensing water from the reaction gas stream when the nitrogen containing compounds can be concentrated in the condensate. Further removal of nitrogen containing compounds can be effected by subsequent treatment with an aqueous wash prior to recovery of the ethylene oxide.

This invention provides a process in which a gas stream from a reaction in which ethylene oxide is produced by reacting ethylene with oxygen which gas stream comprises oxides of nitrogen and steam is cooled preferably in a zone to which no liquid is introduced to form a condensate comprising at least 70% and preferably at least 80% for example at least 90% of water by weight, condensed water is removed and ethylene oxide is then recovered from the gas stream.

Figure 2:
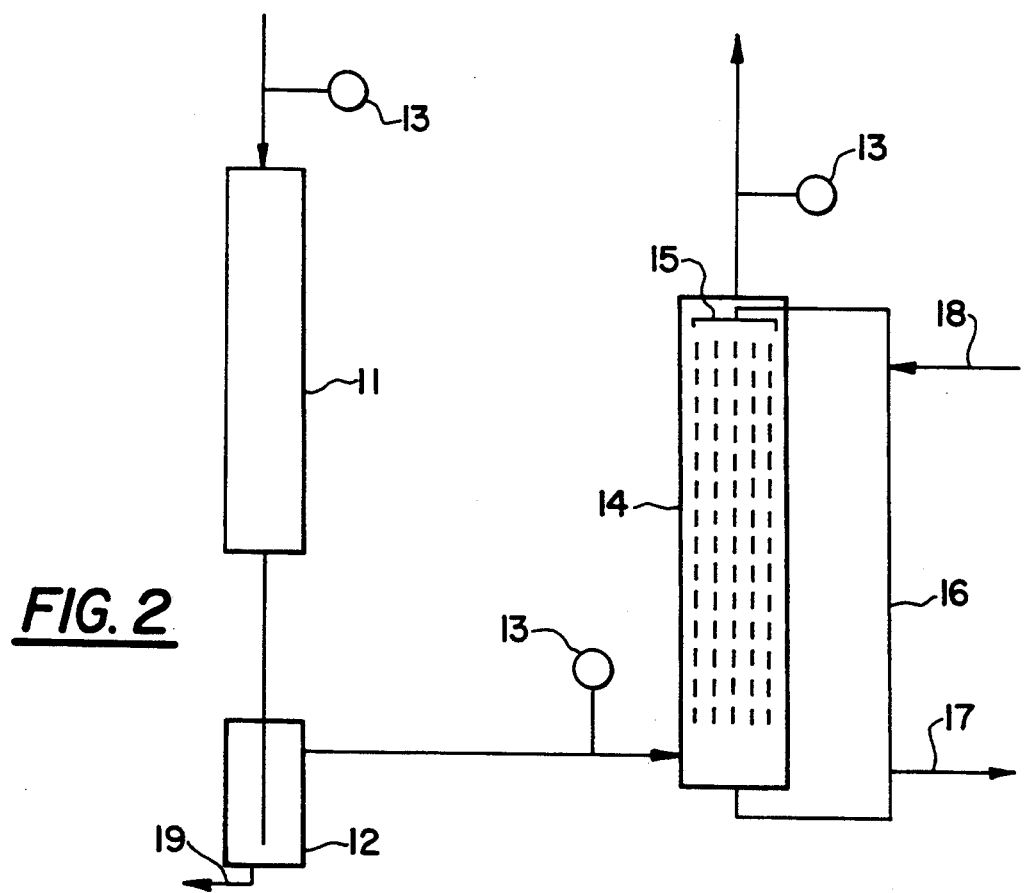

In the accompanying drawings, FIGS. 1 and 2 are diagrammatic illustrations of apparatus and process for carrying out the invention.

In order to secure the required water content of the condensate steam may if necessary be added as such or in the form of droplets comprising water and optionally are alkaline but which preferably comprise only volatile substances and more preferably consist of water only which are substantially completely evaporated before the condensation step. However, the requisite water content may usually be secured by an appropriate amount of cooling.

It is desirable that no added liquid be present during the condensation stage. We believe without wishing to be bound by this explanation that such added liquid is antagonistic to the production of a desirable misty condition of the gas stream otherwise produced during the condensation and which is very efficient in the removal of oxides of nitrogen. Aqueous mist present in the incoming gas stream may be beneficial in itself but difficult to control.

After the condensation step and before the recovery of ethylene oxide the gas stream may be contacted with a stream comprising water for example an aqueous alkali solution or preferably water free from alkali, preferably as a spray to wash impurities from it.

The oxides of nitrogen may comprise NO, $NO_2$, $N_2O_4$, $N_2O_3$ and/or $N_2O_5$ and organic nitrogen containing compounds can include nitromethane, 2-nitroethanol and nitroethylene.

We have found that this procedure is remarkably effective in that a surprisingly high proportion of the nitrogen containing compounds in the gas stream are removed in the condensed water and a subsequent wash with water or alkali will not only remove other impurities but will also more easily bring the remaining concentration of oxides of nitrogen down to an acceptable level. The condensation treatment is especially effective in removing organic nitrogen containing compounds from the gas stream. As the reaction gases will normally contain from 0.1 to a few hundred parts per million and usually at most 50 parts per million, for example 0.5 to 30 parts per million by volume of oxides of nitrogen, the condensation step need cause little hydration and loss of ethylene oxide. Below 50 parts per million of the reaction gas by volume the loss of ethylene oxide is small.

Typically the nitrogen containing compounds in the condensate will comprise about 80% (as nitrogen) of organic nitrogen containing compounds and 40% as inorganic nitrogen containing compounds, principally $NO_x$ compounds.

The condensate and/or any stream comprising water from a contact stage may be heated as a liquid to cause reaction of ethylene oxide contained in it to ethylene glycol suitably at a temperature of 150° to 230° C. and preferably 170° to 210° C. and subsequently distilled in one or more stages to recover pure mono ethylene glycol and optionally di- and higher ethylene glycols from it. In the course of this treatment oxides of nitrogen and organo nitrogen compounds tend to react to form heavy nitrogen containing residues which are easily separated. Any light nitrogen containing species which may be present are also readily removed in the distillation. Advantageously, the condensate may be used for example as spray to the contact stage.

It is desirable that the gas stream from the reaction should comprise 0.1, particularly 0.5, to 5% and especially 0.7 to 2.5% by volume of steam. It is further desirable that the gas stream from the reaction should contain steam at a partial vapour pressure of 50 to 350 mm Hg (6.7 to 46.7 kPa) and particularly 80 to 220 mmHg (10.7 to 29.3 kPa). During condensation it is particularly desirable that the partial vapour pressure of the water is reduced by 20 to 300 mmHg (2.7 to 40 kPa). Suitably the gas stream is cooled from a reaction temperature of for example 190° to 280° C. and particularly 210° to 270° C. to 10° to 80° C. preferably 11° to 80° C. and especially 15° to 60° C.

Any contacting of the gas with an aqueous alkali solution may be carried out conventionally. A less severe treatment may be possible in some cases since some impurities other than oxides of nitrogen may be removed during the condensation, but it may be at least as severe as in conventional processes in which no oxides of nitrogen are present. Suitably the gas stream is contacted with 0.01 to 5% and preferably 0.05 to 0.5% of its own volume of an alkali solution, for example a sodium and/or potassium hydroxide and carbonate solution, preferably having a pH of 7.1 to 9.5 and more preferably 7.5 to 9 as finely divided droplets with a residence time of the gas 0.05 to 30 seconds. If contacting with a stream of water is carried out as aforesaid, the conditions are suitably similar to those using aqueous alkali except that the pH is lower. Contacting with a stream of aqueous alkali or water may also be carried out by passing the gas stream through the liquid for example as such or as liquid flowing over porous packing. The temperature of the stream of contact liquid is suitably 10° C. to 40° C.

Water or alkali solution, as the case may be, may be recirculated to the contact stage thereby increasing their content of ethylene oxide and glycol, improving their suitability for treatment as aforesaid to recover ethylene glycol. We believe that such organic materials and other organic materials for example acetaldehyde and formaldehyde present in the water or alkali solution may also assist in the removal of oxides of nitrogen. Ethylene oxide can then suitably be removed from the gas stream conventionally by absorption into water and desorption to recover the ethylene oxide. The water is preferably re-used in the absorption stage several times and used water treated for recovery of ethylene glycol and its oligomers and polymers. The gas after removal of ethylene oxide may be treated to remove at least part of the carbon dioxide produced as a by product of the process and recycled to the process.

The reaction producing ethylene oxide may be carried out as described in European Patent Specification 0003642 which is incorporated herein by reference. The nitrate or nitrite forming compounds described therein other than oxides of nitrogen are converted at least in part to oxides of nitrogen in the process, and this may be at least to some extent part of the mechanism by which nitrates and nitrites are formed in the process.

The following Examples illustrate the invention. All percentages and parts per million (ppm) of gas streams are by volume.

EXAMPLE 1

One form of the invention will now be described with reference to the accompanying FIG. 1.

Ethylene oxide reactor 1 feeds a cooler 2 from which a cooled pipe passes to alkali contactor 4, which comprises means to spray an aqueous alkaline solution through incoming gas 5 and means to remove sprayed gas 6 and means 7 to recover alkali solution and to recycle part thereof together with fresh solution to the alkali contactor, part of the used alkali solution is rejected through purge line 8. Sample points 3 are provided in appropriate positions. Fresh alkali is added through line 9.

A gas stream comprising:

| Ethylene | 30% |
| Oxygen | 6.5% |
| Carbon Dioxide | 1% |
| Methane | 62.5% |
| Ethyl Chloride | 5 ppm |
| NO/NO$_2$ | 12 ppm |
| Water Vapour | 25 mm Hg (approx) (ca. 3.3 kPa) | was fed to reactor 1 at a rate of 48 m$^3$.hr$^{-1}$ and at a pressure of 15 bar and the reactor was held at an average temperature of 234° C. The reactor contained 9 liters of a catalyst comprising silver supported on porous $\alpha$-alumina pellets.

The gas flowing from the reactor contained 2.1% of ethylene oxide, 0.8% of steam and 9.7 parts per million oxides of nitrogen and about 95 mm Hg (ca. 12.7 kPa) pressure of water vapour. The selectivity of the reaction under these conditions, expressed as moles of ethylene oxide produced per hundred moles of ethylene consumed, was 87%. The temperature of the gas stream was reduced to about 60° C. in the cooler at which temperature no condensation occurred, and the temperature was further reduced to 30° C. in the cooled pipe before passing to the alkali contactor. The concentration of oxides of nitrogen fell to 3.5 ppm at this point, the vapour pressure of water having fallen by at least 50 mmHg (ca. 6.7 kPa) due to condensation. The cooled pipe from cooler 2 to contactor 4 slopes so that the condensate is drained into the sump of contactor 4. The condensate contains more than 80% of water by weight.

The alkali contact solution had a pH of 8 to 8.5, the alkali being added as 1% sodium hydroxide in an amount sufficient to maintain the pH in that range with rejection of a corresponding amount of recovered alkali solution. The solution was sprayed through the gas at a rate of 140 liters per hour.

EXAMPLE 2

A second form of the invention will now be described with reference to FIG. 2 in which an ethylene oxide reactor 11 containing 95 ml of ethylene oxide catalyst comprising silver on an $\alpha$-alumina support feeds a 1 liter volume catch pot 12 (equipped with a drain 19) which passes gas to an alkali contactor 14 equipped with means to recover and recycle alkali solution 16 similar to 4 and 7 of FIG. 1 respectively, 17 is a purge line, 15 is spray means and 13 represents gas sample points. Fresh alkali is introduced through line 18.

A gas stream of composition

| Ethylene | 30.8% |
| Oxygen | 7.8% |
| Nitrogen | 60.9% |
| Carbon Dioxide | 0.5% |
| Ethyl Chloride | 5.0 ppm |
| NO/NO$_2$ | 15.0 ppm | is passed into the reactor at a rate of 660 l.hr$^{-1}$ and a pressure of 15.3 bar and the catalyst maintained at an average temperature of 232° C. The selectivity (moles of ethylene oxide produced per 100 moles of ethylene consumed) of 86.8% was obtained at an exit ethylene oxide concentration of 2.1%.

The exit gas is passed into the catch pot 12 of which the temperature is about 25° C. Condensate collected from the catch pot daily will typically contain about 35% of the nitrogen in the total oxides of nitrogen in the exit gas from the reactor, as tested over a prolonged period (28 days). The burden of oxides of nitrogen to be removed in the alkali contactor 14 is thus substantially reduced. The condensate in the catch pot typically comprises at least 80% water.

The alkali contactors continue to remove aldehydes and organic acids effectively.

EXAMPLE 3 TO 7

Process gas comprising ethylene (30%), oxygen (8%), nitric oxide (15 ppm), ethyl chloride (5 ppm), carbon dioxide (1%) and nitrogen (balance), was passed at 162 l.hr$^{-1}$ corresponding to a gas hourly space velocity of 3000 hr$^{-1}$ through a silver catalyst (50 g, 54.2 ml) heated to a temperature (225° C.) sufficient to generate 2% ethylene oxide in the product gas. The product gas was passed through a condenser externally cooled with a flowing water and equipped with a vessel into which the condensate collected. The said at least partially cooled product gas was next passed to a quench unit comprising a facility to scrub it by spraying with a cooled recirculating aqueous quench stream. The quench functions as a direct contact heat exchanger further cooling the product gas stream thereby effecting further condensation of any water vapour therein. The recirculating quench stream is purged to avoid overloading the quench thereby providing a liquid-stream comprising useful products such as ethylene oxide and ethylene glycol together with by products such as nitrite, nitrate, acetaldehyde formaldehyde, formic acid, bicarbonate, etc. The process was operated at 15 bar. Examples 3 to 7 were operated for about 3 days. The temperature of the condenser cooling water was controlled and measured.

In Example 4, 5 and 7, water vapour was introduced into the product stream immediately on leaving the catalyst bed at a point where the process-side temperature was 225° C. In each case the water introduced was vaporised. In Examples 3 and 6, no water was added.

In all cases the product gases were cooled, the condensate collected, removed and treated before disposal.

In Examples 6 and 7, the temperature of the condenser cooling water was increased from 15° C. to 30° C. The operating conditions and the collection of condensate are summarised in Table 1 below.

EXAMPLE 8 AND 9

The equipment described in Example 1 was fitted additionally with a drain in the pipe connecting condenser 2 with the sump of contactor 4.

Ethylene was converted to ethylene oxide as in Example 1 whilst differing methods of operating the condenser and quench were characterised in terms of the extraction of nitrogen-containing by-products into the condensate and quench liquor. The operating conditions and the collection of condensate are summarised in Table 2 below.

EXAMPLE 10

Example 1 was repeated except that the contactor 4 was operated without addition of alkali. The procedure was to collect condensate from cooler 2 and to pass it through the cooled pipe to contactor 4. In the absence of fresh alkali through line 9, the collected condensate was pumped to spray 5 via means 7 for recycle. Part of the used condensate was continuously bled out through puree line 8. A sample of quench blend or purge from line 8 (1 l, 117 mmol of total N-containing compounds, 71 mmol of 2-nitroethanol, pH 3.1) was concentrated by distilling off water at 70°–80° C. under reduced pressure to yield concentrate A (120 ml, 101 mmol of total N-containing compounds, 47 mmol of 2-nitroethanol, pH 3.4). Concentrate A was loaded into a 300 ml stainless steel cylinder fitted with a thermocouple. The cylinder was purged with helium gas to displace air, sealed and heated by immersion in a temperature programmed oven. Heating to 185° C. took 30 minutes. The temperature was held at 185° C. for 30 minutes and thereafter the cylinder was heated to 200° C. over the following 35 minutes. On cooling to ambient temperature, the pyrolysed concentrate was analysed as comprising 33 mmol of total N-containing compounds including less than 0.02 mmol of 2-nitroethanol. Concentrate B was centrifuged and the supernatant liquid distilled under a partial vacuum using a 360 simulated Vigreux reflux column and a reflux head. A nitrogen bleed maintained an inert atmosphere. The reflux ratio was about 5:1. Pure MEG (mono ethylene glycol) (38 ml) was collected. The boiler temperature was between 145° and 150° C., whilst the pressure was about 100 mmHg (ca. 13.3 kPa).

TABLE 1

|  | Example | | | | |
| --- | --- | --- | --- | --- | --- |
|  | 3 | 4 | 5 | 6 | 7 |
| Condenser cooling water temp. (°C.) | 15 | 15 | 15 | 30 | 30 |
| Water of reaction (% v/v of product gas leaving the reactor) | 0.6 | 0.6 | 0.6 | 0.6 | 0.6 |
| Steam injected (% v/v of product gas leaving the reactor) | 0.0 | 1.8 | 3.0 | 0.0 | 1.8 |
| Total water content of product gas admitted to condenser (% v/v) | 0.6 | 2.4 | 3.6 | 0.6 | 2.4 |
| Water content of product gas leaving condenser (% v/v) | 0.22 | 0.18 | 0.14 | 0.29 | 0.29 |
| Water condensed (ml) | 38 | 147 | 261 | 27 | 135 |
| Nitrogen compounds collected in condensate (% admitted to condenser) | 40 | 47 | 53 | 8 | 21 |

TABLE 2

|  | Example No | |
| --- | --- | --- |
|  | 8 | 9 |
| Condenser temp. (°C.) | 50 | 22 |
| Water condensation rate in condenser (g.hr$^{-1}$) | 0 | 790 |
| Rate of collection of N-contg. by product in condensate (mole % N in oxides of nitrogen fed to reactor) | 0 | 21 |
| Quench liquor circulation (l.hr$^{-1}$) | 70 | 0 |
| Quench temp. (°C.) | 46 | 27 |
| Rate of condensation of water in quench (g.hr$^{-1}$) | 24 | 15 |
| Collection rate of N-containing by products in quench liquor (mole % of N in oxides of nitrogen fed to reactor) | 7 | 6 |

We claim:

1. A process in which a gas stream from a reaction in which ethylene oxide is produced by reacting ethylene with oxygen which gas stream comprises oxides of nitrogen and steam is cooled to form a condensate comprising at least 70% of water by weight, condensed water is removed and ethylene oxide is then recovered from the gas stream and wherein, after the condensation step and before the recovery of ethylene oxide, the gas stream is contacted with a stream comprising a spray of an aqueous solution of an alkali to wash impurities from it.

2. A method as claimed in claim 1 wherein the condensate comprises at least 80% of water by weight.

3. A method as claimed in claim 1 wherein the gas stream comprising oxides of nitrogen and steam is cooled to form a condensate in a zone to which no liquid is introduced.

4. A method as claimed in claim 1 wherein the gas stream is cooled so as to generate a mist of water.

5. A method as claimed in claim 1 wherein the condensate is used as spray to the contact stage.

6. A method as claimed in claim 1 wherein the gas stream from the reaction comprises from 0.1 to 5% by volume of steam.

7. A method as claimed in claim 1 wherein the gas stream from the reaction comprises steam at a partial vapour pressure of 50 to 350 mm Hg (6.7 to 46.7 kPa).

8. A method as claimed in claim 1 wherein the partial vapour pressure of the water is reduced by 20 to 300 mm Hg (2.7 to 40 kPa).

9. A method as claimed in claim 1 wherein the gas stream is cooled from a reaction temperature of from 190° to 280° C. to a temperature of from 10° to 80° C.

10. A process in which a gas steam from a reaction in which ethylene oxide is produced by reacting ethylene with oxygen which gas stream comprises oxides of nitrogen and steam is cooled to form a condensate comprising at least 70% of water by weight, condensed water is removed and ethylene oxide is then recovered from the gas stream and wherein, after the condensation step and before the recovery of ethylene oxide, the gas stream is contacted with a stream comprising a spray of an aqueous solution of an alkali to wash impurities from it.

11. A method as claimed in claim 10 wherein the condensate comprises at least 80% of water by weight.

12. A method as claimed in claim 10 wherein the gas stream comprising oxides of nitrogen and steam is cooled to form a condensate in a zone to which no liquid is introduced.

13. A method as claimed in claim 10 wherein the gas stream is cooled so as to generate a mist of water.

14. A method as claimed in claim 10 wherein the condensate is used as spray to the contact stage.

15. A method as claimed in claim 10 wherein the gas stream from the reaction comprises from 0.1 to 5% by volume of steam.

16. A method as claimed in claim 10 wherein the gas stream from the reaction comprises steam at a partial vapour pressure of 50 to 350 mm Hg (6.7 to 46.7 kPa).

17. A method as claimed in claim 10 wherein the partial vapour pressure of the water is reduced by 20 to 300 mm Hg (2.7 to 40 kPa).

18. A method as claimed in claim 10 wherein the gas stream is cooled from a reaction temperature of from 190° to 280° C. to a temperature of from 10° to 80° C.

* * * * *